United States Patent
Yoshikawa et al.

(10) Patent No.: US 12,078,627 B2
(45) Date of Patent: Sep. 3, 2024

(54) MEASUREMENT METHOD AND MEASUREMENT DEVICE USING GAS SENSOR

(71) Applicant: NATIONAL INSTITUTE FOR MATERIALS SCIENCE, Ibaraki (JP)

(72) Inventors: Genki Yoshikawa, Ibaraki (JP); Takahiro Nemoto, Ibaraki (JP); Masaaki Matoba, Ibaraki (JP); Kosuke Minami, Ibaraki (JP)

(73) Assignee: NATIONAL INSTITUTE FOR MATERIALS SCIENCE, Ibaraki (JP)

( * ) Notice: Subject to any disclaimer, the term of this patent is extended or adjusted under 35 U.S.C. 154(b) by 351 days.

(21) Appl. No.: 17/627,421

(22) PCT Filed: Jun. 17, 2020

(86) PCT No.: PCT/JP2020/023663
§ 371 (c)(1),
(2) Date: Jan. 14, 2022

(87) PCT Pub. No.: WO2021/014835
PCT Pub. Date: Jan. 28, 2021

(65) Prior Publication Data
US 2022/0260540 A1    Aug. 18, 2022

(30) Foreign Application Priority Data

Jul. 25, 2019    (JP) .................................. 2019-137069

(51) Int. Cl.
*G01N 33/00*    (2006.01)
*G01N 1/38*    (2006.01)

(52) U.S. Cl.
CPC ........... *G01N 33/0036* (2013.01); *G01N 1/38* (2013.01); *G01N 2001/381* (2013.01)

(58) Field of Classification Search
None
See application file for complete search history.

(56) References Cited

U.S. PATENT DOCUMENTS

| 2013/0133433 A1 | 5/2013 | Yoshikawa et al. |
| 2020/0121222 A1* | 4/2020 | Becker ............... A61B 5/093 |
| 2020/0249201 A1 | 8/2020 | Shiba et al. |

FOREIGN PATENT DOCUMENTS

| DE | 102010014222 A | * 10/2011 | ......... G01N 33/0031 |
| EP | 1 205 748 | 5/2002 | |

(Continued)

OTHER PUBLICATIONS

Office Action issued Nov. 15, 2023 in corresponding Chinese Patent Application No. 202080050969.3, with English translation.

(Continued)

*Primary Examiner* — Daniel S Larkin
(74) *Attorney, Agent, or Firm* — Wenderoth, Lind & Ponack, L.L.P.

(57) ABSTRACT

The present invention suppresses an adverse effect caused when an additional gas such as water vapor is mixed in a sample gas or the like that is subjected to gas measurement. In an embodiment of the present invention, in gas measurement for analyzing sensor output signals obtained by alternately supplying a sample gas and a reference gas to a sensor element while alternately switching between the sample gas and the reference gas, the sample gas and the reference gas pass through a humidity equilibration device partitioned by a water vapor permeable membrane, and then are supplied to the sensor element. As a result, since both gases have substantially the same value of humidity at the time of being supplied to the sensor element, influences of water vapor are substantially cancelled out in signals output from the sensor element by the alternate supply of the sample gas and the reference gas.

20 Claims, 8 Drawing Sheets

(56) References Cited

FOREIGN PATENT DOCUMENTS

| | | | |
|---|---|---|---|
| JP | H0961352 A | * | 3/1997 |
| JP | 2007-170982 | | 7/2007 |
| WO | 2011/148774 | | 12/2011 |
| WO | 2018/221283 | | 12/2018 |

OTHER PUBLICATIONS

International Search Report issued Sep. 1, 2020 in corresponding International Application No. PCT/JP2020/023663.
N. Trivett et al., World Meteorological Organization Global Atmosphere Watch, "Guide on Sampling and Analysis Techniques for Chemical Constituents and Physical Properties in Air and Precipitation as Applied at Stations of the Global Atmosphere Watch Part 1: Carbon Dioxide", (https://library.wmo.int/pmb_ged/wmo-td_980_en.pdf), 1999, with English translation and cited in the specification.
Extended European search report issued Jul. 26, 2023 in corresponding European Patent Application No. 20843648.5.
Official Letter dated Apr. 19, 2024 issued in corresponding European patent application No. 20843648.5, 7 pages.
Second Office Action dated Jun. 4, 2024 in corresponding Chinese patent application No. 202080050969.3, with English translation, 12 pages.

* cited by examiner

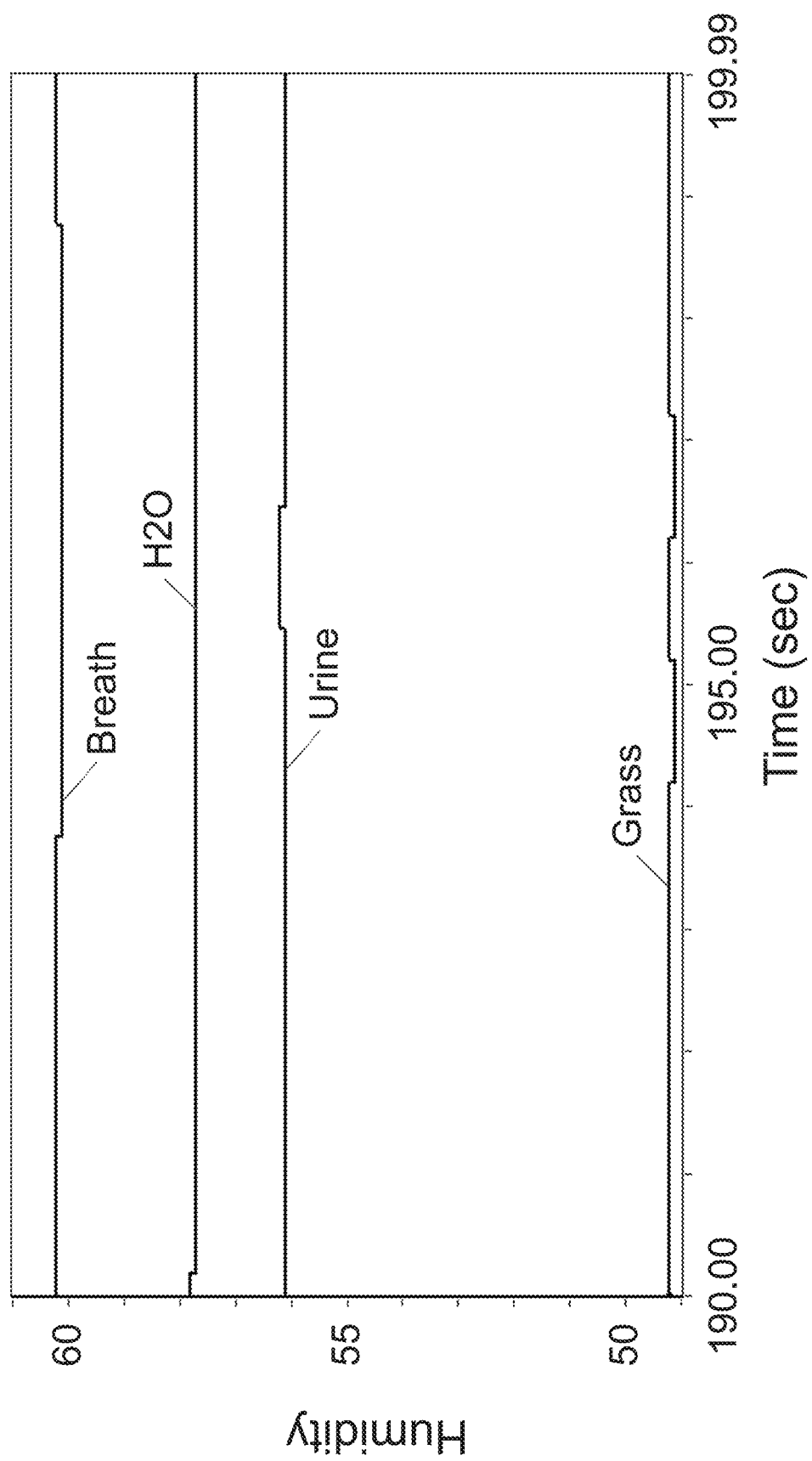

MEASUREMENT METHOD AND MEASUREMENT DEVICE USING GAS SENSOR

CROSS-REFERENCE TO RELATED APPLICATIONS

This application is a U.S. national stage application of the PCT International Application No. PCT/JP2020/023663 filed on Jun. 17, 2020, which claims the benefit of foreign priority of Japanese Patent Application No. 2019-137069 filed on Jul. 25, 2019, the contents of which are incorporated herein by reference in their entirety.

TECHNICAL FIELD

The present invention relates to a measurement method using a gas sensor, particularly to a measurement method for removing an influence of a specific gas (for example, water vapor or oxygen) in a sample gas or a reference gas as much as possible. The present invention also relates to a measurement device that performs such a measurement method.

BACKGROUND ART

Gas sensors are widely used for measuring components in extremely various gases such as various gases generated from animals including humans, plants, automobiles, industrial equipment, factories, and houses, environmental gases such as the atmosphere, and others (also including a gas generated by volatilization or the like from a solid, a liquid, or a solution even when a substance is normally in a state of solid, liquid, or being dissolved in a liquid) and others. One of the problems to be solved in measurement of such a gas is to remove or reduce an influence of water vapor contained in the gas on a measurement result. A large amount of water is present in nature, and a large amount of water vapor is contained in an exhaust gas of an internal combustion engine or the like in a device or the like manufactured by a human. In addition, a large amount of water is used in factories and houses, and water vapor is generated by combustion or the like. In this manner, a gas to be measured (hereinafter, also referred to as a sample gas) often contains a large amount of water vapor. Such a large amount of water vapor in a sample gas may make it difficult to detect gas sensor output signals derived from other components in the sample gas, particularly derived from trace components, or presence of water vapor may affect a detection result of other components. Furthermore, for example, when a harmful gas mixed in the outside air is detected or the amount of the harmful gas is measured, the amount of water vapor in a sample gas can often change depending on circumstances or the like, for example, the humidity of the outside air largely changes depending on weather or the like, which further complicates the problem.

In order to eliminate the above-described adverse effect caused by water vapor present in a sample gas, various countermeasures have been conventionally considered and used for actual measurement. Non-Patent Literature 1 relates to a specific method and device for measuring carbon dioxide in the atmosphere, and Non-Patent Literature 2 is a Japanese translation of almost the entire text of Non-Patent Literature 1, although partially omitted. In Section 2.2.3 "Gas Drying" of Non-Patent Literature 2, it is described that water vapor in a sample gas affects a measured value of carbon dioxide and that dehumidification from the sample gas is necessary. Section 2.2.3.1 "Cryocooler method" immediately below this section describes a method for removing water vapor by cooling a sample gas to condense water vapor in the sample gas, and section 2.2.3.2 "Desiccant" describes a method for removing water vapor by causing a sample gas to pass through an appropriate chemical desiccant such as magnesium chloride. Furthermore, Section 2.2.3.3 "Ion exchange membrane (Nafion membrane)" describes a method for causing air containing a sample gas to pass through a Nafion tube made of a membrane of Nafion (registered trademark), which is a hygroscopic ion exchange material that is a kind of perfluorosulfonic acid polymer, and at this time, causing a tube wall to absorb water vapor to perform dehumidification. Here, moisture absorbed by the Nafion tube passes through the Nafion tube and evaporates to be released to the outside. In order to efficiently release the absorbed moisture, it is also described that a sufficiently dry gas for carrying away water vapor is supplied from the outside. Furthermore, 2.2.3.4 "Method of Constant Water Vapor Pressure" of Non-Patent Literature 2 describes a method for performing humidification such that a water vapor pressure of each of a sample gas and a calibration gas for measurement calibration is a saturated vapor pressure of a certain constant temperature within a range of 2 to 4° C., and then causing these gases to pass through dehumidifying tubes maintained at the same temperature, respectively.

All of these methods described with reference to Non-Patent Literature 2 (Non-Patent Literature 1) are intended to eliminate an influence of water vapor in a sample gas on a carbon dioxide measurement result as much as possible by reducing the humidity of the sample gas to a constant value close to 0% as much as possible. It is considered that these methods provide good results in terms of accurately and stably measuring various components in a sample gas as long as components other than water vapor in the sample gas are not affected. However, in the above methods, since operation and treatment of bringing the humidity in the sample gas to a constant value close to 0% are performed, the device configuration, control, and the like therefore tend to be large and complicated. Therefore, the above methods are not necessarily satisfactory when application to portable measurement devices required to be downsized, various small devices required to incorporate such measurement devices, and low-cost devices required to have a simple structure and a simple control procedure is considered.

As one of sensors that can be used for a gas sensor, a surface stress sensor has been studied in recent years. In particular, in Patent Literature 1, a Membrane-type Surface stress Sensor (MSS) is proposed and studies thereof have progressed. In the MSS, a periphery of a silicon membrane, extending in a two-dimensional direction such as a circular shape or a square shape, is supported from four directions, and a surface stress generated on the silicon membrane is concentrated on these support portions, thereby extremely high sensitivity and high mechanical stability can be achieved as compared with a conventional surface stress sensor having a cantilever shape. In normal gas measurement using a surface stress sensor, a receptor layer that generates a surface stress by adsorbing a desired component is applied to a surface of the surface stress sensor (a surface of a silicon membrane a periphery of which is supported at four points in the MSS), and a sample gas and a reference gas (also referred to as a purge gas) are alternately and periodically exposed to such an applied surface stress sensor. Temporally changing surface stresses applied to the surface of the surface stress sensor to which the receptor has been applied are received as output signals of the surface stress sensor, and the signals are analyzed by various methods to determine the kind, amount, ratio, and the like of a component in the sample gas.

FIG. 1 shows a block diagram of a configuration example of the gas measurement device according to related art as described above. A carrier gas and a reference gas are supplied to mass flow controllers MFC1 and MFC2, respectively, from the left side of the diagram. The mass flow controllers MFC1 and MFC2 operate alternately (that is, in opposite phases) to perform alternate periodic feeding of the above-described two kinds of gases. That is, these mass flow controllers alternately repeat a feed phase and a stop phase at a predetermined cycle usually set to several seconds to several tens of seconds. In addition, in a time section in which one mass flow controller is operating in a feeding phase for feeding a supplied gas at a predetermined flow rate, the other mass flow controller is in a stop phase in which feeding of a gas is stopped.

A carrier gas fed from the mass flow controller MFC1 is supplied to a first vial containing a liquid or solid sample containing a volatile component, and a headspace gas containing the volatile component present in a headspace of the first vial is pushed out toward a second vial on a downstream side as a sample gas. Meanwhile, the reference gas fed from the MFC2 is supplied to the second vial. A flow path of the sample gas and a flow path of the reference gas are integrated in the second vial and supplied to a sensor chamber containing a sensor element such as a surface stress sensor.

Note that FIG. 1 only shows a configuration example of the gas measurement device, and there may be various other configurations, which are currently used. For example, in a configuration example shown in FIG. 3, a solid or liquid containing a volatile component is assumed as a sample, but a gaseous sample from the beginning may be used. In this case, means for appropriately mixing the gas sample with the carrier gas may be arranged instead of the first vial, or the sample gas may be supplied to the mass flow controller MFC1 from the beginning instead of the carrier gas. The carrier gas is preferably a gas that does not affect measurement of a sample gas, or a gas that can remove an influence thereof on a measurement result from the measurement result even if the gas affects the measurement result, for example, because the influence is known. In addition, the carrier gas is preferably a gas that does not obstruct various members on a flow path or a sensor for measurement. As the carrier gas, for example, the same gas as a reference gas can be used. As the reference gas, a nitrogen gas, a rare gas such as argon, or the atmospheric air is usually used. In addition, in this configuration example, although the flow path of the carrier gas and the flow path of the reference gas are integrated in the second vial, a mechanism or the like that actively performs switching between the flow paths, such as a switching valve, is not arranged in the second vial itself, and the switching is controlled by gas supply-stop operations in phases opposite to each other performed by the mass flow controllers MFC1 and MFC2. However, switching of a gas to the sensor chamber can also be performed by another configuration or control procedure. For example, the second vial can be replaced with a flow path switching mechanism such as a valve, although not intended to be limited thereto. Note that, in this case, instead of arranging the mass flow controllers MFC1 and MFC2 on an upstream side of the switching mechanism, it is advantageous to appropriately arrange a pump that draws a gas from the upstream side and feeds the gas to a downstream side of the flow path switching mechanism at a desired flow rate on the downstream side, that is, on an outlet (exhaust) side of the sensor chamber, between the switching mechanism and the sensor chamber, in the sensor chamber, or the like. In addition, the sensor chamber can contain not only the gas sensor element but also any additional member. Examples of such an additional member include, but are not limited to, a sensor element that measures various parameters such as humidity and temperature of a gas in the sensor chamber, an electric circuit, a computer, and other arithmetic/storage devices for performing various treatments such as control, diagnosis, power supply, and output amplification of a sensor element and other various members, and performing various arithmetic treatments, an element for providing an interface for communication or the like between the sensor chamber and the outside thereof, and an element for heating/cooling.

In a gas sensor, since there are a large number of kinds of gas components to be detected, various kinds of responsiveness of a receptor layer are required. However, the receptor layer generates a surface stress by adsorbing a component in a sample gas, but a receptor layer material often adsorbs not a single chemical species of gas but a plurality of (often very diverse) chemical species of gases, and often adsorbs water vapor at a ratio that cannot be ignored in addition to a desired chemical species. Of course, there are also receptor layer materials with very low responsiveness to water vapor. However, as described above, it is desired to provide a receptor layer having various kinds of responsiveness. Therefore, if possible, it is highly beneficial if a receptor that exhibits high responsiveness to water vapor can also be used to measure a sample gas that may contain a large amount of water vapor.

Furthermore, even a gas other than water vapor may affect a result of gas measurement due to presence of a specific gas in a sample gas. Elements arranged in various gas sensors such as a receptor of a surface stress sensor and selectively responding to a gas component to be measured often respond to various gases. In such a case, presence of a specific gas in a sample gas may adversely affect detection of another gas as in the case of water vapor. For example, a gas generated by natural environments and various human activities often contains a significant amount of oxygen, and a large amplitude response to this oxygen may be included in sensor output signals. However, it is difficult to almost completely remove oxygen and the like from a sample gas in gas measurement. Moreover, for example, since the oxygen concentration of exhaled breath of humans or animals or that of an exhaust gas generated as a result of combustion of fuel is not necessarily constant, even if an influence of a specific gas on measurement can be separately quantified and compensated by post-treatment of a measurement result, it is not so easy to implement this. The "specific gas" is not limited only to a single component gas such as water vapor or oxygen, and also includes a mixture of a plurality of kinds of gases. Furthermore, with respect to the reference gas, the specific gas as described above may also unavoidably or unintentionally come to be mixed in, it is desirable to be able to easily cope with such a situation.

SUMMARY OF INVENTION

Technical Problem

An object of the present invention is, in a gas sensor that performs measurement while alternately switching between a reference gas and a sample gas over a plurality of cycles, such as a surface stress sensor, to eliminate or reduce an influence of a specific gas such as water vapor that is allowed to be contained in the sample gas.

Solution to Problem

An aspect of the present invention provides a measurement method using a gas sensor, the measurement being performed while switching between a reference gas and a sample gas to be measured and supplying the reference gas and the sample gas to a sensor element in the gas sensor, in which at least one of the reference gas and the sample gas is allowed to contain a specific gas, the method comprising a step of equilibrating a concentration of the specific gas in the reference gas supplied to a sensor element in the gas sensor with a concentration of the specific gas in the sample gas are equilibrated.

Here, the concentration of the specific gas in the reference gas and the concentration of the specific gas in the sample gas may be equilibrated by connecting a flow path of the reference gas and a flow path of the sample gas to each other via a permeable membrane for the specific gas.

The flow path of the reference gas and the flow path of the sample gas may be connected to each other via a structure constituted of the permeable membrane, an additional permeable membrane, and an additional gas existing therebetween.

The additional gas may be a gas having the same composition as the reference gas.

The permeable membrane may contain at least one of a material that reversibly absorbs and releases the specific gas and a material having a hole that allows the specific gas to pass therethrough.

The material having a hole that allows the specific gas to pass therethrough may be a hollow fiber membrane.

The material that reversibly absorbs and releases the specific gas may be a material selected from the group consisting of a perfluorosulfonic acid polymer and a vinyl alcohol-based polymer.

The sensor element may be a sensor element that detects a surface stress.

The sensor element that detects a surface stress may be a membrane-type surface stress sensor element.

The specific gas may be water vapor.

Another aspect of the present invention provides a gas measurement device for performing any one of the above measurement methods, in which the device comprises a reference gas source, means for obtaining a sample gas to be measured, and means for supplying a reference gas from the reference gas source and the sample gas to a sensor element with alternately switching therebetween.

Advantageous Effects of Invention

According to the present invention, it is possible to largely reduce an influence of a specific gas such as water vapor in a sample gas only by performing minimum addition and improvement on a conventional measurement device. In addition, as a member to be added, basically, a movable member that functions during a period in which an operation for reducing an influence of the specific gas is performed or a member that performs an active operation is not required, and there is usually no need to perform a process or control such as some kind of detection.

BRIEF DESCRIPTION OF DRAWINGS

FIG. 5B shows a graph showing measurement results of Example of the present invention.

DESCRIPTION OF EMBODIMENTS

Figure 1:
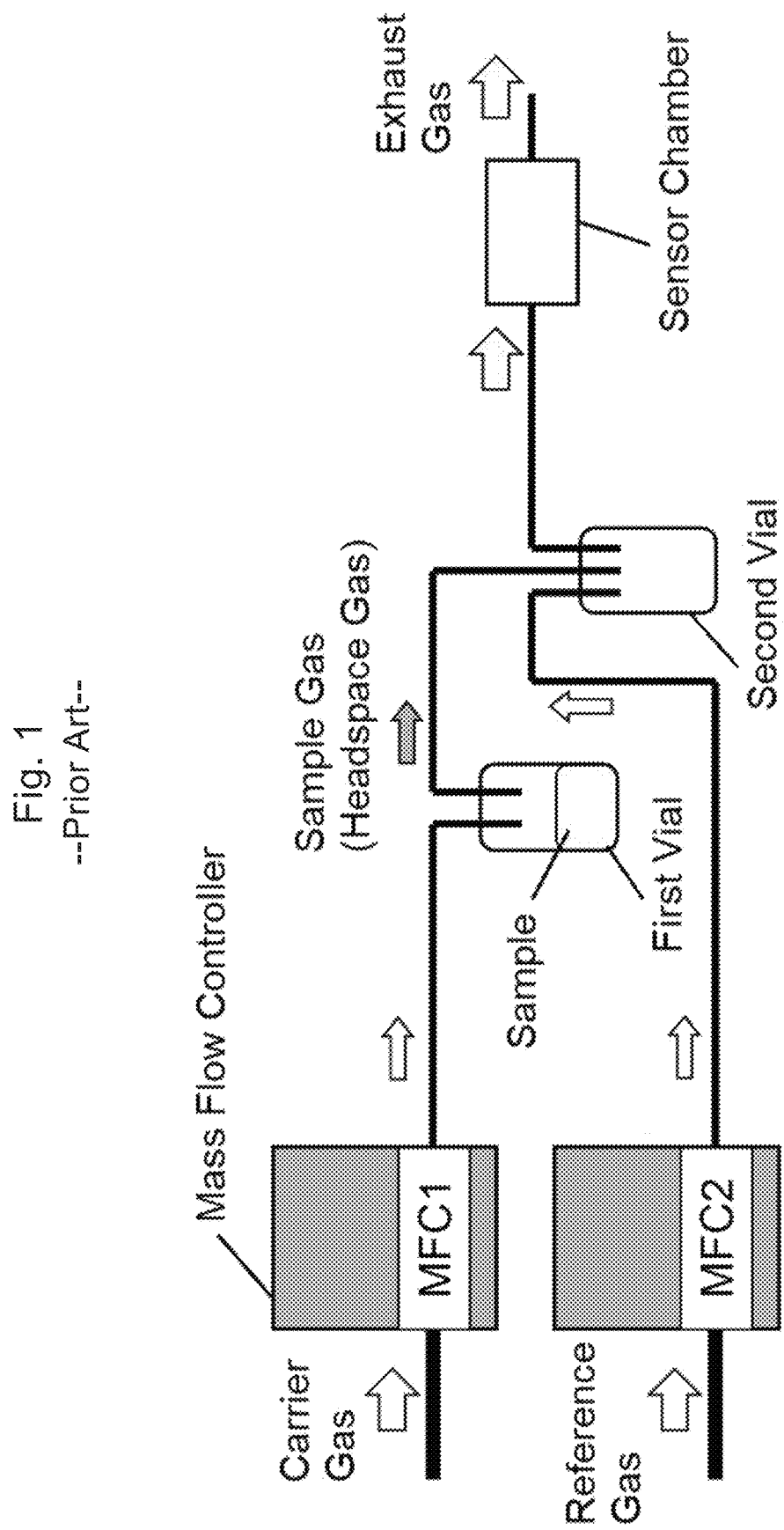
FIG. 1 is a conceptual illustration of a configuration example of a gas measurement device according to related art.

The present invention does not specify the kind of the above-described specific gas in a reference gas and/or a sample gas, but in the following, water vapor is exemplified the specific gas, and description will be given assuming that the specific gas may be contained in the sample gas. However, as a person skilled in the art can easily understand, the description of such a specific case does not lose generality.

According to an embodiment of the present invention, in a gas sensor that performs measurement while alternately switching between a reference gas and a sample gas to supply the reference gas and the sample gas to a sensor element, such as a surface stress sensor, the humidity of the reference gas and the humidity of the sample gas are equilibrated by connecting a flow path of the reference gas and a flow path of the sample gas via a water vapor permeable membrane such as a Nafion membrane, instead of using a device or a method for setting the amount of water vapor (humidity) in the sample gas to a value near zero or equal to or less than a predetermined threshold close to zero. As a result, each of the humidities of the reference gas and the sample gas after the humidity equilibrium is not necessarily a constant value due to the amount of water vapor in the original sample gas; however, in a measurement result of the reference gas and a measurement result of the sample gas (usually, both are not constant values but temporally changing signals) in each switching cycle of both gases, influences of water vapor in the gases on the gas sensor are substantially the same as each other. Therefore, the influences of water vapor are so-called direct current components in both measurement results. Since the direct current component appearing in a measurement result is usually ignored as a simple direct current offset also in a conventional measurement method for performing this kind of alternate switching measurement, by removing the direct current offset from the measurement result signal by alternate measurement in a similar manner to the conventional method, the influences of water vapor after equilibrium appearing in both the reference gas measurement cycle and the sample gas measurement cycle can be easily canceled out.

It should be noted here that it theoretically takes infinite time for the humidities of the reference gas and the sample gas connected via such a water vapor permeable membrane to reach an equilibrium state in a strict sense. In an actual measurement, it is not possible to wait for an infinite time for this equilibration. In the present application, it is assumed that the humidity equilibrium is reached at a time point when the humidity of the reference gas and the humidity of the sample gas are sufficiently close to each other, and a measurement result is substantially the same as a measurement result in a case of complete equilibrium. Furthermore, it should be noted that the present invention also encompasses, for example, a case where, even when the humidities of both gases are in a partial or incomplete equilibrium state, that is, even when the equilibrium is not completely achieved in the above sense, a more useful measurement result than that before the equilibration treatment is performed is obtained by bringing the humidities of both gases closer to each other than those before the equilibration treatment starts (for example, by reducing a humidity difference of 50%, in which the initial humidities were 0% and 50%, to a humidity difference of 5%, in which the humidities were 22.5% and 27.5%, by the equilibration treatment), or a useful measurement result is finally obtained by combining the reduction in humidity difference by the equilibration treatment with another treatment or a treatment after the measurement result is obtained.

Figure 2:
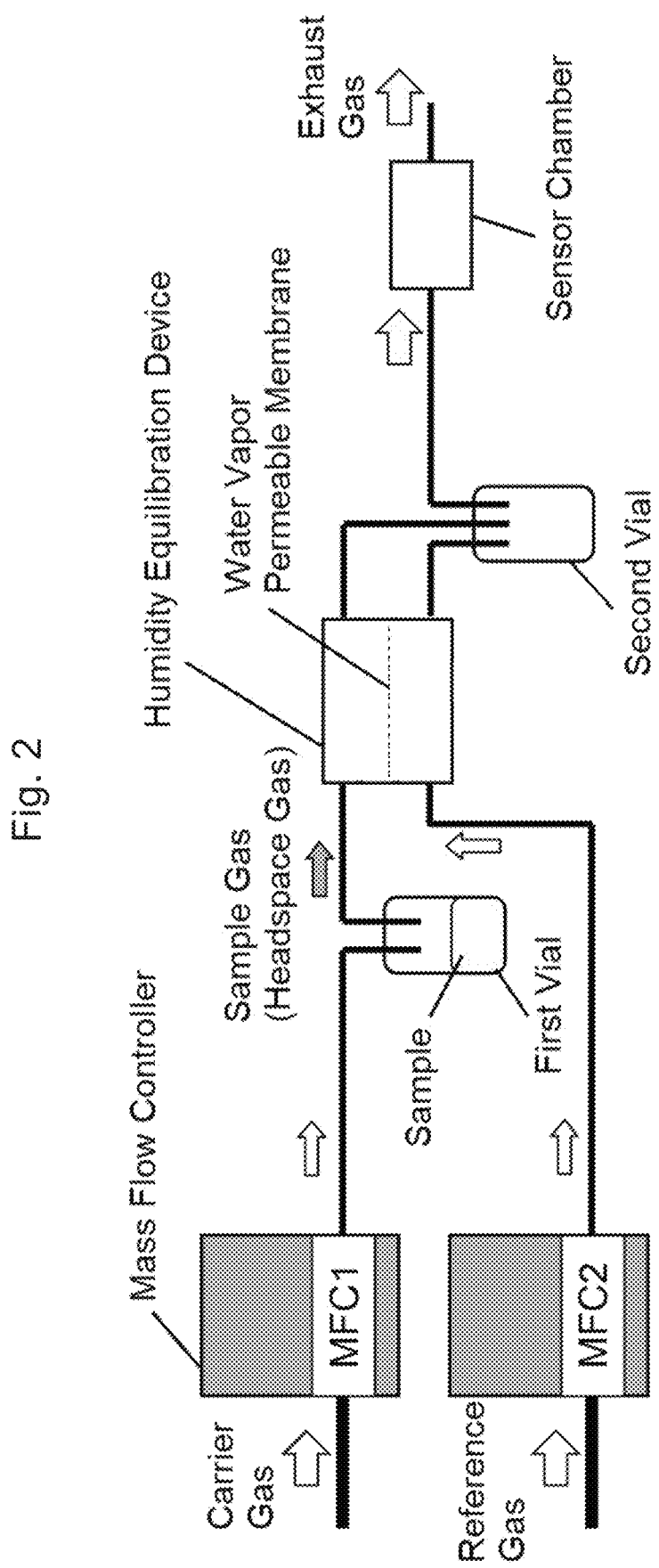
FIG. 2 is a conceptual illustration of a configuration example of a gas measurement device according to the present invention.

A configuration example of a gas measurement device capable of performing the above-described measurement is conceptually shown in FIG. 2. In the conceptual illustration shown in FIG. 2, a humidity equilibration device that equilibrates the humidity of the reference gas and the humidity of the sample gas, as described above, is inserted into the conceptual illustration of the conventional gas measurement device shown in FIG. 1. In the humidity equilibration device, a water vapor permeable membrane is arranged between a flow path of the reference gas and a flow path of the sample gas. Water vapor moves from a high humidity side to a low humidity side via the water vapor permeable membrane, and the humidities of both gases thereby asymptotically approach an equilibrium state. Note that in FIG. 2, the humidity equilibration device is drawn to have a simple box-like structure the inside of which is divided by a partition wall (water vapor permeable membrane) on a plane, but this is a conceptual structural illustration drawn in an extremely simplified manner for the sake of clarity. In an actual humidity equilibration device, in order to achieve humidity equilibrium with high efficiency in a limited space, various modifications may be made such as increasing the area of the water vapor permeable membrane, for example, by forming the water vapor permeable membrane into a pipe-like structure, and naturally, this kind of any modification remains within the technical scope of the present invention.

In the configuration of the present invention as shown in FIG. 2, an insertion position of the humidity equilibration device is on the flow paths of the reference gas and the sample gas and in a section where the flow path of the sample gas and the flow path of the reference gas are separated from each other. That is, the insertion position is up to an integration point (the second vial in FIG. 2) of the flow paths on a downstream side, and up to a point where the humidity of the sample gas does not substantially change on an upstream side. More specifically, in relation to the upstream side, a section from a supply source (not shown) of the carrier gas to the first vial is connected to a flow path on a downstream side of the first vial, and water vapor may be contained in a head space gas in the first vial. Therefore, there is no guarantee that the amount of water vapor contained in the carrier gas on the upstream side is the same as that contained in the sample gas on the downstream side of the first vial. In addition, when water vapor may be mixed or absorbed on a path even on a downstream side of the first vial or an element corresponding thereto, the humidity equilibration device is preferably arranged on a downstream side of a place where such a phenomenon occurs.

Regarding the water vapor permeable membrane that brings the reference gas and the sample gas into contact with each other, in principle, any membrane can be used as long as the membrane has water vapor permeability and finally has low permeability and absorbability for a component to be detected in the sample gas enough to achieve a purpose of measurement such as detection or identification of an object to be measured. In addition, in principle, a contact portion may have any specific shape or size. However, in a normal application, humidity equilibrium between the reference gas and the sample gas desirably occurs in a time as short as possible, and in order to avoid an increase in the size of the device, a volume occupied by the contact portion is desirably small.

Therefore, for example, Nafion or another perfluorosulfonic acid polymer can be used as a material of the membrane. The chemical structural formula of Nafion is shown below.

[Chemical Formula 1]

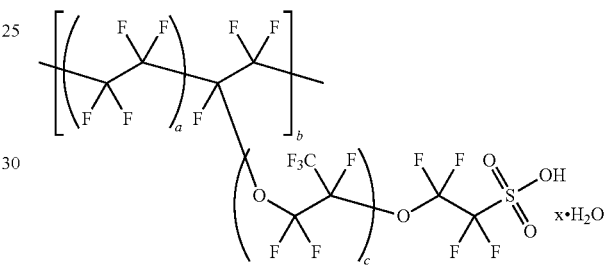

Since Nafion has a complicated nanostructure, causes and the like of the characteristics of Nafion have not been completely clarified. As one model, it is presumed that Nafion forms a cluster in which reverse micelles formed of a perfluoroalkyl ether group having a hydrophilic sulfonic acid and each having a diameter of about 4 nm are connected to each other. A reason why an ability to absorb moisture and other protic substances is high despite a high proportion of a hydrophobic moiety is considered to be that ions and water can be transported by this network coated with a sulfonic acid group. Nafion has such characteristics, and is therefore a preferable material as the water vapor permeable membrane used in the present invention. A perfluorosulfonic acid polymer other than Nafion can be used similarly. For example, several kinds of perfluorosulfonic acid polymers each having a chemical structure and physical properties similar to Nafion, for example, Flemion (registered trademark) manufactured by Asahi Glass Co., Ltd. and Aciplex (registered trademark) manufactured by Asahi Kasei Corporation are commercially available, and these other perfluorosulfonic acid polymers can also be used similarly.

In addition, for example, a hygroscopic material capable of reversibly absorbing, releasing, and permeating water vapor, such as a vinyl alcohol-based polymer film, can be used, and among such hygroscopic materials, a material having a high water vapor absorption, release, and permeation rate is preferable, although not intended to be limited thereto. Further, even a material that is not hygroscopic, such as a hollow fiber membrane or a nanomaterial membrane having a large number of extremely minute pores through which a water molecule passes, can also be used. Moreover, the water vapor permeable membrane is not limited to those formed only of the above materials. For example, when it is difficult to form membranes from the above-described materials themselves or the above-described materials themselves are likely to be broken, dissolved, or the like during use even if the materials can be formed into membranes, a material serving as a frame for supporting each of these materials to provide a tough membrane as a whole or a material for forming a composite material modified such that a tough membrane can be easily formed can also be contained in the water vapor permeable membrane.

In addition, in order to achieve a rapid equilibrium between the reference gas and the sample gas, the membrane preferably has a large area. In order to increase the area of the membrane at a boundary between both gases in a limited space, the membrane desirably has a non-flat three-dimensional shape. Such a structure and shape are often seen in a device for performing gas exchange or heat exchange. For example, it is possible to adopt a structure in which at least a part of a wall surface of an inner tube out of tubes having a double structure is made of the water vapor permeable material, one of the reference gas and the sample gas flows in the inner tube, and the other gas flows between an outer tube and the inner tube to equilibrate the humidity in the inner tube and the humidity in the outer tube.

Furthermore, instead of bringing the reference gas and the sample gas into direct contact with each other via the water vapor permeable membrane, an additional gas and an additional water vapor permeable membrane may be interposed between the reference gas and the sample gas. In this case, a gas contact structure of "reference gas/water vapor permeable membrane/third gas/water vapor permeable membrane/sample gas" is formed. In this structure, by using a dried gas as the third gas, the humidities of the reference gas and the sample gas when reaching an equilibrium can be further lowered. In the above-described case, only one structure of "/third gas/water vapor permeable membrane/" is arranged, but of course this structure may be repeated a plurality of times. In addition, as the kind of the third gas, the same gas as the reference gas may be used. As described above, the contact between the reference gas and the sample gas via the water vapor permeable membrane is not direct but indirect in that an additional gas is also interposed therebetween, and a gas to be detected in the sample gas can be thereby prevented or reduced from leaking to the reference gas side. As a result, it is possible to reduce a decrease in sensitivity caused by a partial cancel out of a detection signal level of a gas to be detected on the sample gas side due to a detection signal of the gas to be detected on the reference gas side, caused by the leakage. Furthermore, in some cases, all or some of components that have leaked into the third gas can be returned to the original sample gas side.

Note that permeation of a gas via the water vapor permeable membrane is normally bidirectional, and therefore it is also necessary to take leakage of the third gas to the sample gas side into account. From this point of view, it is often preferable to use the same kind of gas as the reference gas as the third gas. Of course, since there are other measures such as using a gas that is unlikely to permeate the water vapor permeable membrane as the third gas, it should be noted that it is not essential that the third gas is the same kind of gas as the reference gas.

Figure 3:
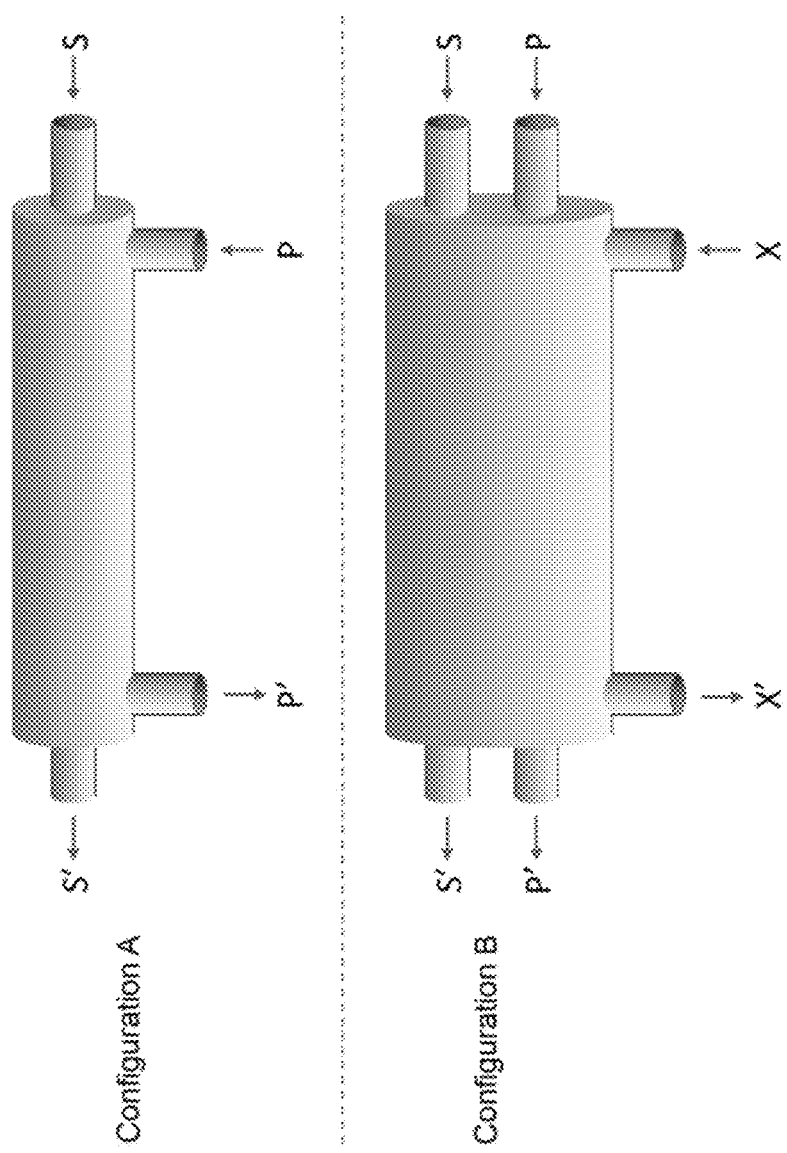
FIG. 3 is an illustration of a configuration example of a humidity equilibration device inserted into a gas flow path in the present invention.

An example of a humidity equilibration device having such a tubular structure is shown in FIG. 3. In FIG. 3, P and P' represent reference gases before and after input thereof into the humidity equilibration device, respectively, S and S' represent sample gases before and after input thereof into the humidity equilibration device, respectively, and X and X' represent third gases before and after input thereof into the humidity equilibration device, respectively. Note that, as described above, FIG. 3 shows that the sample gas flows through a thin tube, but conversely, the reference gas may flow through a thin tube.

In configuration A in FIG. 3, an inner tube out of the double tubes is formed of the water vapor permeable membrane, and the sample gas and the reference gas flow into a space in the inner tube and a space between the inner and outer tubes, respectively, to equilibrate the humidity of the sample gas and the humidity of the reference gas. Note that, in the illustrated configuration, the volume of the space in the inner tube and the volume of the space between the inner and outer tubes may be substantially the same as each other, or one may be larger than the other. For example, if the volumes of both spaces are the same as each other, the humidity of each of the gases at an outlet of the humidity equilibration device can be an arithmetic average of the original humidity of each of the gases under conditions where the tubes are long enough to reach equilibrium sufficiently. Alternatively, when the reference gas side is a dry gas, by increasing the volume of the space between the inner and outer tubes, the humidity of each of the gases at the outlet of the humidity equilibration device can be lower than the arithmetic average value. When an actual device is designed, it is only required to appropriately adjust absolute values and ratios of the volumes of both spaces so as to satisfy various requirements required for measurement.

Configuration B in FIG. 3 shows an example of a configuration for performing humidity equilibrium of a type in which the reference gas and the sample gas are indirectly brought into contact with each other via the third gas by arranging the above-described third gas and an additional water vapor permeable membrane. In this configuration, the reference gas and the sample gas flow into two inner tubes formed of the water vapor permeable membranes, respectively, and a thicker outer tube surrounding both tubes is arranged to cause the third gas to flow into a space between the inner tube and the outer tube. As a result, water vapor is exchanged between the reference gas and the sample gas in the two inner tubes via the third gas, and humidity equilibrium thereby occurs between both gases.

Note that when dehumidification is performed in a tube system using these water vapor permeable membranes, a configuration is usually adopted in which the direction of a gas flow in the inner tube and the direction of a gas flow in the outer tube are opposite to each other. However, in order to ensure equilibration of humidity in the present invention, conversely, in many cases, it is considered that it is preferable to align the directions of both gas flows in the same direction. Of course, the directions of both gas flows can be opposite to each other. More generally speaking, it should be noted that the present invention does not limit the relative direction of the two gas flows via the water vapor permeable membrane to any particular one.

In addition, in order to further increase the area of the water vapor permeable membrane, a plurality of inner tubes may be arranged inside the outer tube. Note that instead of increasing the membrane area for the sample gas humidity equilibration by causing the same sample gas to pass through the plurality of inner tubes in the common outer tube arranged in this manner, different sample gases may pass through some of the inner tubes, or the kind of sample gas may differ depending on an inner tube. In this manner, for example, a humidity equilibration device for gas measurement for a plurality of sample gases can be integrated. Note that, in this case, it is desirable that a kind of crosstalk between the plurality of inner tubes, that is, an influence of erroneous detection caused by passing of a component to be detected in a certain sample gas through the water vapor permeable membrane and entering of the component into another sample gas flowing in another inner tube falls within an error range required for the measurement.

As another non-limiting example of the humidity equilibration device, there is a bundle of tubes or other flow paths, for example, in which figures of a plurality of polygonal shapes such as a honeycomb shape and a lattice shape, a circle, and other various shapes in cross section are joined to each other. If a structure of a rectangular assembly having adjacent cross sections will be described as an example, it is possible to efficiently equilibrate humidity by preparing a bundle of flow paths in which a plurality of tubes or the like having rectangular cross sections is arranged in parallel (of course, a wall portion between adjacent tubes may be a single wall that partitions a space in the adjacent tubes instead of a double structure in which side walls of the tubes overlap each other) and causing different gases to flow through flow paths having adjacent side surfaces.

Figure 4:
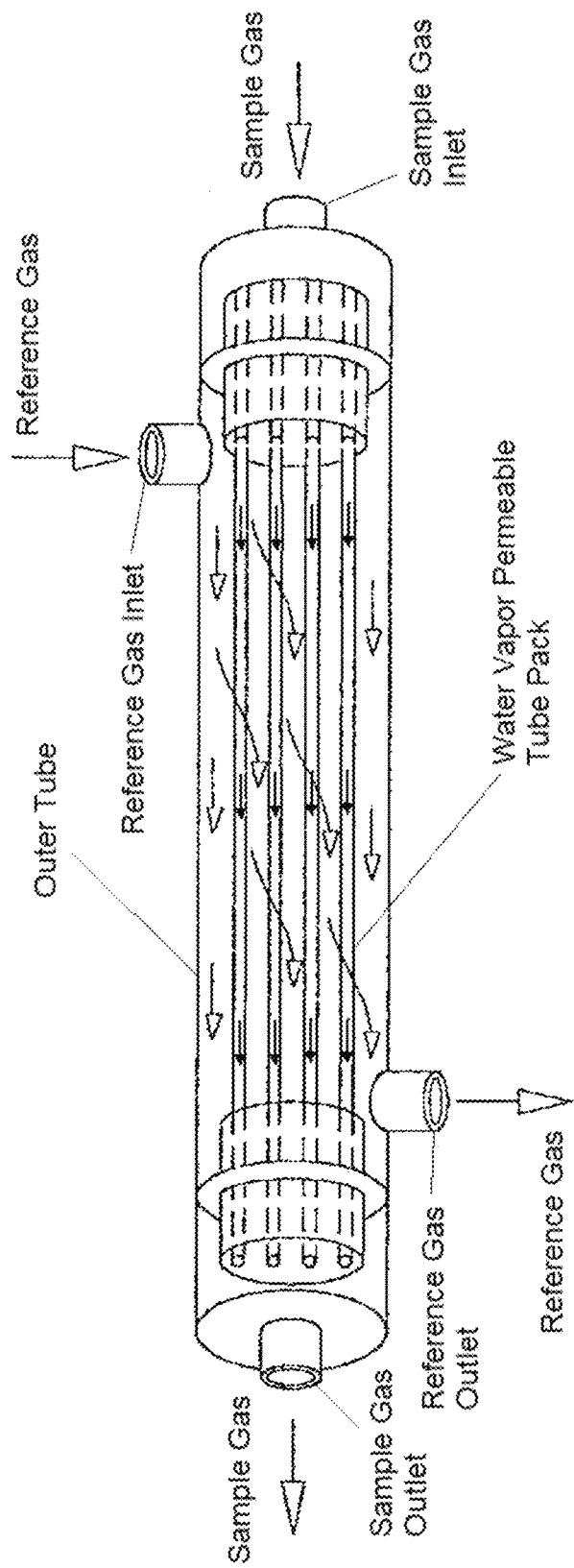
FIG. 4 is an illustration showing a more specific configuration example of the humidity equilibration device inserted into a gas flow path in the present invention.

An example of a more specific structure of the humidity equilibration device shown in configuration A in FIG. 3 formed in this manner is shown in FIG. 4. In FIG. 4, the sample gas is introduced from a sample gas inlet at the right end of the humidity equilibration device shown as a conceptual illustration, enters a water vapor permeable tube pack arranged inside the humidity equilibration device and obtained by bundling tubes each having a tube wall made of a water vapor permeable material, is divided into a plurality of tubes in the water vapor permeable tube pack, and flows from the right to the left in an outer tube of the humidity equilibration device. Meanwhile, the reference gas is introduced into the outer tube from a reference gas inlet located near the right end of the water vapor permeable tube pack near the upper right in FIG. 4, and flows in the same direction as the sample gas in the water vapor permeable tube pack, that is, from the right to the left in FIG. 4. When the humidity of the reference gas is lower than the humidity of the sample gas, water vapor in the sample gas permeates a tube wall of each of tubes of the water vapor permeable tube pack due to a humidity gradient between the sample gas and the reference gas, and enters the reference gas flowing through a space between the water vapor permeable tube pack and the outer tube. Conversely, when the humidity of the reference gas is higher than the humidity in the sample gas, water vapor in the reference gas enters the sample gas via the water vapor permeable tube pack. Of course, it is also possible to reverse the flow paths of the sample gas and the reference gas. Note that this naturally holds true for examples described below. Note that the water vapor permeable tube pack in FIG. 4 is shown as a bundle of four tubes, but naturally, the number of tubes may be appropriately set as necessary.

When the number of tubes in the water vapor permeable tube pack is increased, the area of a water vapor permeable membrane surface increases, and therefore the outer tube can be shortened, but the diameter thereof increases. As another consideration matter, through the water vapor permeable membrane, a sample gas component gas other than water vapor may also pass (leak). Therefore, when the area of the water vapor permeable membrane is excessively large, the amount of a gas to be detected in the sample gas leaking to the reference gas side cannot be ignored in some cases. When the amount of such a gas to be detected leaking to the reference gas side cannot be ignored, not only by a decrease in a detection signal level due to a decrease in the amount of a gas to be detected in the sample gas, but also by detection of a gas to be detected in the reference gas, a detection signal level of the gas to be detected in the sample gas is canceled out, which further decreases sensitivity. Therefore, it cannot be said that the larger the area of the water vapor permeable membrane such as the total extension of the water vapor permeable tube is, the better. The area of the water vapor permeable membrane is desirably set within an appropriate range in consideration of a balance between the water vapor passing amount and the leakage amount of a gas to be detected.

Note that when the flows of the reference gas and the sample gas on a surface of the water vapor permeable membrane are completely laminar flows, a time during which water vapor transported from one of the gases to the other gas via the water vapor permeable membrane retains on the membrane surface is long. Therefore, water vapor transport efficiency is low, and it takes a long time until humidity equilibrium is achieved. In order to avoid this, preferably, by peeling off an airflow near the surface from the surface such that a certain degree of turbulence occurs near the surface, a gas from which water vapor has been carried away via the membrane due to being present near the water vapor permeable membrane or water vapor transported via the water vapor permeable membrane is immediately mixed with a surrounding gas. For this purpose, it is only required to arrange a protrusion, a cutout, or another structure that disturbs an air flow on or near the surface of the water vapor permeable membrane, or to form the shape of the water vapor permeable membrane itself (in the above-described example, the shape of the tube itself formed of the water vapor permeable membrane) such that a laminar flow is easily peeled off from the surface. However, since excessive turbulence may cause turbulence such as pulsation or irregular vibration in a flow of the reference gas and/or the sample gas to be sent to the gas sensor, which may cause noise in a signal from the gas sensor, a configuration should be made in consideration of this point.

In addition, in the configuration of the measurement device shown in FIG. 2, since the mass flow controllers MFC1 and MFC2 on the sample gas side and the reference gas side perform on/off operation in phases opposite to each other, gas flows in the sample gas side region and the reference gas side region in the humidity equilibration device are basically pulsatile gas flows that perform on/off operation in phases opposite to each other. For this reason, as compared with a case where the flow rates of both gas flows flowing across the water vapor permeable membrane are substantially constant, the efficiency of humidity equilibration by the membrane may decrease, or the efficiency of humidity equilibration may temporally change in synchronization with switching of both gases, and as a result, the humidities of both gases may also temporally change (it should be noted that, conversely, there is a time during which a gas flow stops for a certain period of time, which may increase the efficiency of equilibration). When such a decrease in efficiency and a temporal change in humidity cannot be ignored, for example, the reference gas and the sample gas can be each supplied to the humidity equilibration device at a constant flow rate (an average flow rate of each of the gases supplied to the sensor chamber, or the like), and by arranging a storage of each of the gases on a downstream side of the humidity equilibration device, each of the above-described gases in phases opposite to each other can be periodically fed from the storage toward the sensor chamber. Alternatively, if it is only necessary to reduce the pulsation to some extent, it is also possible to arrange a smoothing means such as a gas container that absorbs a pulsation of a flow rate by having a certain volume (which may further have a shape serving as a resistance of a gas flow) upstream or downstream of the humidity equilibration device. In this case, the humidity equilibration device itself also has a certain volume at a place through which each of the gases passes, and also has resistance to a gas flow due to inclusion of a pipe through which the gases pass. Therefore, the humidity equilibration device itself can also serve as the smoothing means. Note that the reference gas, the sample gas, and the like may be each supplied at any flow rate, and not only the temperature, pressure, concentration, and the like of each of the gases at this time can be arbitrarily selected, but also it is not all the time necessary to alternately and repeatedly supply and stop the sample gas and the reference gas, that is, any condition can be applied.

In addition, if the magnitude of a sensor response to the same component is largely affected by the water vapor amount, sufficient accuracy may not be achieved only with the humidity equilibrium between the reference gas and the sample gas as described above in the case where an absolute value of the magnitude of the sensor response is required. However, such a case can be addressed by, for example, providing a humidity sensor (and, in addition, a temperature sensor, as necessary) in the sensor to which the reference gas and the sample gas are supplied, and holding the data in the measurement system in the form of a table or the like for compensating the influence of humidity (or, temperature in addition) on the magnitude of a response of a component in question. That is, when a certain component is identified in measurement, by performing compensation based on the above-described compensation data on the apparent amount of the component, the accuracy of quantitative measurement of the component can be increased. Note that, in the above description, the humidity sensor is arranged in the sensor (the sensor chamber in the example shown in FIG. 2) to which the reference gas and the sample gas are supplied. However, the position where the humidity sensor is arranged is not limited to this position as long as the humidity at the position is the same as that in the sensor chamber. More specifically, such a humidity sensor may be arranged between the integration point of the reference gas and the sample gas and the sensor chamber, an inside of the sensor chamber, or in a downstream side of the sensor chamber as long as the humidity sensor is arranged on an upstream side of a portion where the humidity may change due to mixing of an additional gas or the like.

Note that, as described above, water vapor has been described as an example of the specific gas, but naturally, the specific gas may be another gas such as oxygen. In addition, the specific gas has been described assuming that this specific gas can be contained in the sample gas side, but the specific gas may also be contained in both the reference gas and the sample gas or only in the reference gas.

EXAMPLES

Hereinafter, Example of the present invention in which water vapor is used as an example of the specific gas will be described. However, it should be noted that the present invention is not limited to this Example, and the technical scope of the present invention is determined based on the claims of the present application.

Figure 5A:
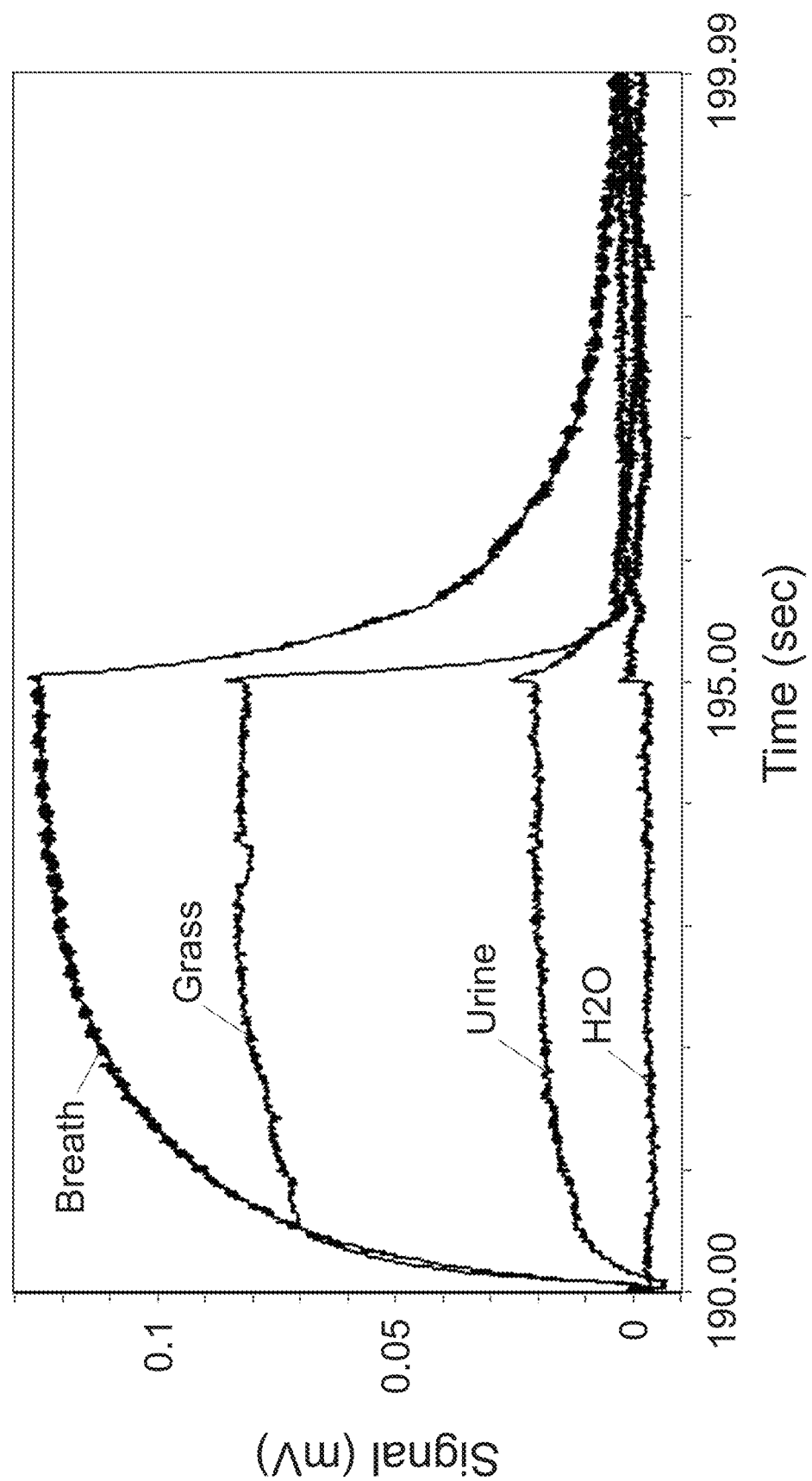
FIG. 5A shows a graph showing measurement results of Example of the present invention.

In the present Example, configuration A shown in FIG. 3 was used as the humidity equilibration device, a Nafion tube was used as the inner tube, and a stainless steel tube was used as the outer tube. Various sample gases passed through the inner tube, and air as a reference gas passed through the outer tube. The sample gas and the reference gas having humidities equilibrated with each other obtained in this manner were supplied to a sensor chamber using MSS as a surface stress sensor. MSS signals thus obtained are shown in FIG. 5A. Here, as the sample gas, "exhaled breath collected in a bag" ("Breath" in FIG. 5A) was used as an example of a gas sample, a head space gas of "leaves of *Houttuynia cordata*" ("Grass" in FIG. 5A) contained in a container was used as an example of a solid sample, and head space gases of "urine" and "water" ("Urine" and "H2O" in FIG. 5A) contained in containers were used as examples of a liquid sample. A series of gas introduction procedures for 10 seconds in which the sample gas is introduced into the sensor chamber for five seconds and then the reference gas is introduced into the sensor chamber for five seconds are defined as one cycle. Each of the gases was introduced for 19 cycles for 190 seconds, and then signals obtained at the 20th cycle are shown in FIG. 5A. FIG. 5B shows a humidity change obtained at the same time. More specifically, FIG. 5B shows signals output from a humidity sensor (not shown in FIG. 3) placed in the sensor chamber. Note that the same applies to FIG. 6B. As can be confirmed by FIGS. 5A and 5B, a variation of an output signal due to humidity can be suppressed by using the present device.

Figure 6A:
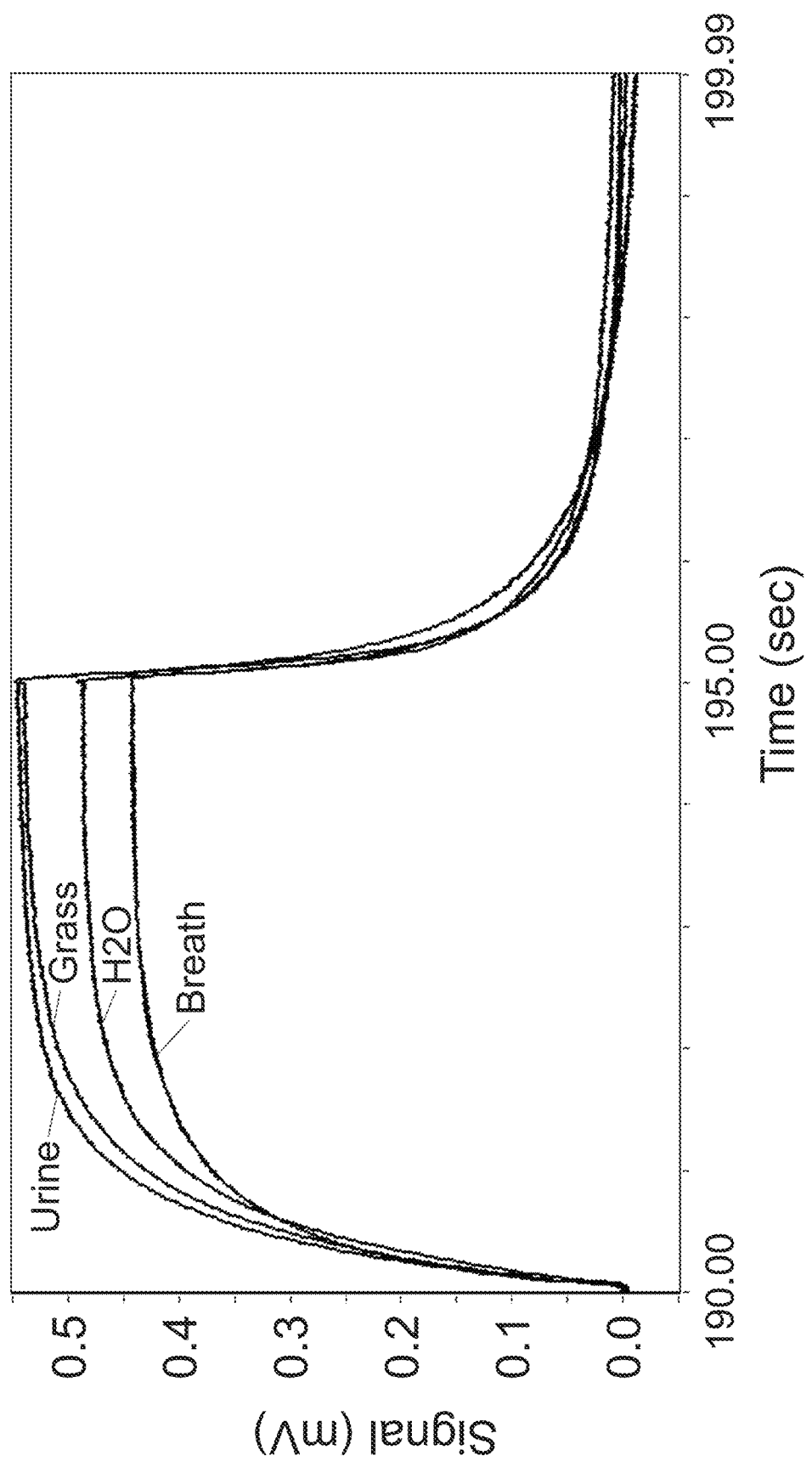
FIG. 6A shows a graph showing measurement results of Comparative Example for comparison and contrast with Example of the present invention.
Figure 6B:
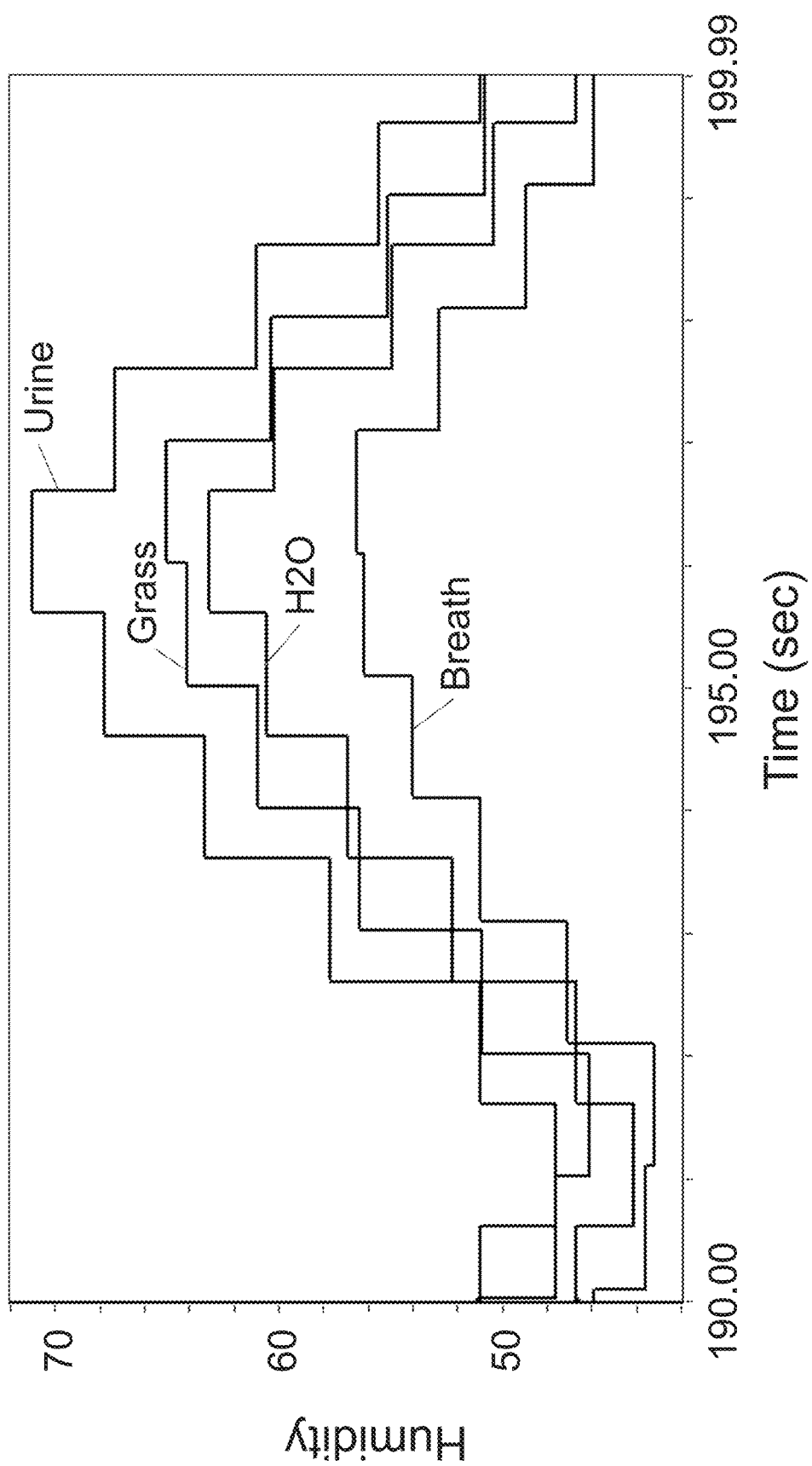
FIG. 6B shows a graph showing measurement results of Comparative Example for comparison and contrast with Example of the present invention.

As a comparative experiment of Example the measurement results of which are shown in FIGS. 5A and 5B, MSS output signals obtained when various sample gases and air as the reference gas are directly introduced into the sensor chamber without using the humidity equilibration device are shown in FIG. 6A. Here, sample gases prepared in the same manner as the experimental procedure of Example shown in FIG. 5A, that is, exhaled breath contained in a bag (Breath), and head space gases of leaves of *Houttuynia cordata* (Grass), urine (Urine), and water (H2O) are used, and MSS output signals obtained at the 20th cycle are shown similarly to the procedure of FIG. 5A. Similarly to FIG. 5B, FIG. 6B shows a humidity change obtained simultaneously with FIG. 6A (note that a response time of the humidity sensor used for the measurement is about several seconds, which is considerably slow). As can be confirmed by FIGS. 6A and 6B, in the case where the present humidity equilibration device is not used, the signals are largely affected by a humidity change.

Here, comparing the graphs each showing a humidity change during one cycle shown in FIGS. 5B and 6B, in Comparative Example of FIG. 6B, humidity given to the sensor (MSS) largely changes along with switching between the reference gas and the sample gas within one cycle for each of the samples. Along with this, in FIG. 6A showing MSS signals, a large amplitude is observed for each of the samples. It should be noted here that, generally, the amplitude of an MSS output signal tends to increase as a measured humidity is higher, and MSS output signal waveforms shown here have shapes very similar to each other. That is, the measurement results of Comparative Example shown in FIGS. 6A and 6B indicate that, in the MSS output signals, a response based on a component unique to a sample is buried in a large response based on a large amount of water vapor contained in a sample gas for each of the samples, and it is not easy to remove the influence of the water vapor from the response and to extract a response of the MSS to the other components.

On the other hand, in FIGS. 5A and 5B, first, as can be seen from FIG. 5B, the measured humidity is substantially constant during one cycle of the MSS output signal from each of the samples. This indicates that humidity equilibrium is achieved between the reference gas and the sample gas. Furthermore, the graphs of the MSS output signals shown in FIG. 5A indicate that correlation between the amplitude of the output signal and a humidity value shown in FIG. 5B is clearly smaller than that in FIGS. 6A and 6B, and furthermore, the waveform of the MSS output signal largely differs depending on a sample. These indicate that by supplying the reference gas and the sample gas having humidities equilibrated with each other via the humidity equilibration device to the MSS to cancel out influences of the humidities in both gases on the output signals, a difference in response of the MSS to a component unique to each of the sample gases other than water vapor clearly appears on the MSS output signals.

INDUSTRIAL APPLICABILITY

As described above, according to the present invention, even when a considerable amount of water vapor is contained in a sample gas, it is possible to largely reduce an influence of water vapor on a measurement result without measuring the amount of water vapor contained in the original sample gas by performing measurement in which the humidities of a reference gas and the sample gas are equilibrated with each other via a water vapor permeable membrane and then the reference gas and the sample gas are alternately and repeatedly supplied to a sensor such as a surface stress sensor. In addition, in order to perform the humidity equilibration treatment, a movable component such as a pump or a valve, an active component, measurement of humidity or the like, and control such as feedback of a result of the measurement are essentially not required. Therefore, since the present invention can reduce a humidity influence while minimizing an increase in size and complexity of a measurement device, the present invention can be largely expected to be used for a portable device, a low-cost device, and the like, although not being limited thereto.

CITATION LIST

Patent Literature

Patent Literature 1: WO 2011/148774 A
Non-Patent Literature
Non-Patent Literature 1: Guide on Sampling and Analysis Techniques for Chemical Constituents and Physical Properties in Air and Precipitation as Applied at Stations of the Global Atmosphere Watch PART 1: Carbon Dioxide (https://library.wmo.int/pmb_ged/wmo-td_980_en.pdf)
Non-Patent Literature 2: WMO Carbon Dioxide Observation Manual (http://ds.data.jma.go.jp/gmd/qasac/report/WMO_CO2_MANUAL_j.pdf)

The invention claimed is:

1. A measurement method using a gas sensor, the measurement being performed while alternately switching between a reference gas and a sample gas to be measured and supplying the reference gas and the sample gas to a sensor element in the gas sensor,
   wherein at least one of the reference gas and the sample gas is allowed to contain a specific gas,
   the method comprising a step of equilibrating a concentration of the specific gas in the reference gas with a concentration of the specific gas in the sample gas by connecting a flow path of the reference gas and a flow path of the sample gas to each other via a permeable membrane for the specific gas,
   wherein a gas flow of the reference gas and a gas flow of the sample gas flowing across the permeable membrane are alternate gas flows by switching between the reference gas and the sample gas.

2. The measurement method using a gas sensor according to claim 1, wherein the flow path of the reference gas and the flow path of the sample gas are connected to each other via a structure constituted of the permeable membrane, an additional permeable membrane, and an additional gas existing therebetween.

3. The measurement method using a gas sensor according to claim 2, wherein the additional gas is a gas having the same composition as the reference gas.

4. The measurement method using a gas sensor according to claim 1, wherein the permeable membrane contains at least one of a material that reversibly absorbs and releases the specific gas and a material having a hole that allows the specific gas to pass therethrough.

5. The measurement method using a gas sensor according to claim 4, wherein the material having a hole that allows the specific gas to pass therethrough is a hollow fiber membrane.

6. The measurement method using a gas sensor according to claim 4, wherein the material that reversibly absorbs and releases the specific gas is a material selected from the group consisting of a perfluorosulfonic acid polymer and a vinyl alcohol-based polymer.

7. The measurement method using a gas sensor according to claim 1, wherein the sensor element is a sensor element that detects a surface stress.

8. The measurement method using a gas sensor according to claim 7, wherein the sensor element that detects a surface stress is a membrane-type surface stress sensor element.

9. The measurement method using a gas sensor according to claim 1, wherein the specific gas is water vapor.

10. The measurement method using a gas sensor according to claim 1, wherein the permeable membrane is arranged on the flow paths of the reference gas and the sample gas and in a section where the flow path of the sample gas and the flow path of the reference gas are separated from each other.

11. A gas measurement device for performing the measurement method according to claim 1, wherein the device comprises:
   a reference gas source;
   means for obtaining a sample gas to be measured;
   means for supplying a reference gas from the reference gas source and the sample gas to a sensor element with alternately switching therebetween; and
   a permeable membrane for the specific gas to connect a flow path of the reference gas and a flow path of the sample gas to each other,
   wherein the gas measurement device is constituted to make a gas flow of the reference gas and a gas flow of the sample gas flowing across the permeable membrane be alternate gas flows by switching between the reference gas and the sample gas.

12. The gas measurement device according to claim 11, wherein the permeable membrane is arranged on the flow paths of the reference gas and the sample gas and in a section where the flow path of the sample gas and the flow path of the reference gas are separated from each other.

13. The gas measurement device according to claim 11, wherein the flow path of the reference gas and the flow path of the sample gas are connected to each other via a structure constituted of the permeable membrane, an additional permeable membrane, and an additional gas existing therebetween.

14. The gas measurement device according to claim 13, wherein the additional gas is a gas having the same composition as the reference gas.

15. The gas measurement device according to claim 11, wherein the permeable membrane contains at least one of a material that reversibly absorbs and releases the specific gas and a material having a hole that allows the specific gas to pass therethrough.

16. The gas measurement device according to claim 15, wherein the material having a hole that allows the specific gas to pass therethrough is a hollow fiber membrane.

17. The gas measurement device according to claim 15, wherein the material that reversibly absorbs and releases the specific gas is a material selected from the group consisting of a perfluorosulfonic acid polymer and a vinyl alcohol-based polymer.

18. The gas measurement device according to claim 11, wherein the sensor element is a sensor element that detects a surface stress.

19. The gas measurement device according to claim 18, wherein the sensor element that detects a surface stress is a membrane-type surface stress sensor element.

20. The gas measurement device according to claim 11, wherein the specific gas is water vapor.

* * * * *